(12) United States Patent
Wang et al.

(10) Patent No.: US 8,563,031 B2
(45) Date of Patent: Oct. 22, 2013

(54) PIROXICAM-CONTAINING MATRIX PATCHES AND METHODS FOR THE TOPICAL TREATMENT OF ACUTE AND CHRONIC PAIN AND INFLAMMATION THEREWITH

(75) Inventors: Changjin Wang, San Diego, CA (US); Eric Y. Sheu, Lafayette, CA (US); Nancy Vuong, San Lorenzo, CA (US)

(73) Assignee: Absize, Inc., Sakai-Shi, Osaka (JP)

( * ) Notice: Subject to any disclaimer, the term of this patent is extended or adjusted under 35 U.S.C. 154(b) by 44 days.

(21) Appl. No.: 13/115,898

(22) Filed: May 25, 2011

(65) Prior Publication Data

US 2011/0293721 A1  Dec. 1, 2011

Related U.S. Application Data

(60) Provisional application No. 61/396,347, filed on May 27, 2010.

(51) Int. Cl.
*A61K 9/70* (2006.01)
(52) U.S. Cl.
USPC .......................................... 424/449; 424/448
(58) Field of Classification Search
USPC ................................................ 424/448, 449
See application file for complete search history.

(56) References Cited

U.S. PATENT DOCUMENTS

2007/0196457 A1*  8/2007  Zhang et al. .................. 424/448

FOREIGN PATENT DOCUMENTS

| EP | 1 366 762 A1 | 12/2003 |
| WO | WO-94/15609 | 7/1994 |
| WO | WO-94/23713 | 10/1994 |
| WO | WO-2005/046654 A1 | 5/2005 |
| WO | WO 2005046654 A1 * | 5/2005 |

OTHER PUBLICATIONS

International Search Report and Written Opinion dated Apr. 19, 2012 in related PCT Application No. PCT/US2011/038189.

* cited by examiner

*Primary Examiner* — Michael G Hartley
*Assistant Examiner* — Micah-Paul Young
(74) *Attorney, Agent, or Firm* — Foley & Lardner LLP

(57) ABSTRACT

This invention relates to matrix patches for the topical (i.e., transdermal) delivery of piroxicam and methods for the treatment of acute and chronic pain and inflammation therewith, particularly pain and inflammation caused by sports injuries or other muscle aches or injuries requiring the application of analgesic and/or anti-inflammation medication, in this instance, piroxicam.

4 Claims, No Drawings

PIROXICAM-CONTAINING MATRIX PATCHES AND METHODS FOR THE TOPICAL TREATMENT OF ACUTE AND CHRONIC PAIN AND INFLAMMATION THEREWITH

CROSS-REFERENCE TO RELATED APPLICATIONS

This application claims priority under 35 U.S.C. §119(e) to U.S. Provisional Application Ser. No. 61/396,347 filed May 27, 2010 which application is incorporated herein by reference in its entirety.

FIELD OF THE INVENTION

This invention relates to matrix patches for the topical (i.e., transdermal) delivery of piroxicam (a well known NSAID) and methods for the treatment of acute and chronic pain and inflammation therewith, particularly pain and inflammation caused by sports injuries or other muscle aches or injuries requiring the application of analgesic and/or anti-inflammation medication, in this instance, piroxicam.

BACKGROUND OF THE INVENTION

Pain represents a large and dynamic market. Non-steroidal anti-inflammatory drugs (NSAIDs) are among the most commonly prescribed drugs worldwide and are responsible for approximately one-quarter of all adverse drug reaction reports. NSAIDs are widely prescribed for patients with rheumatic disease, a population at increased risk for serious gastrointestinal (GI) complications. Topical administration of NSAIDs offers the advantage of local, enhanced drug delivery to affected tissues with a reduced incidence of systemic adverse effects, such as peptic ulcer disease and GI hemorrhage. Thus, treating pain topically is preferred as it delivers the active drug molecules to where the pain and inflammation are locally and avoids the so-called first-pass metabolism thus minimizing systemic exposure and adverse effects. There is growing physician and patient interest in and demand for prescription therapies that can deliver safe, effective and convenient site-specific pain management.

There are many technical challenges in topically delivering drugs through skin. NSAIDs administered topically penetrate slowly and in small quantities into the systemic circulation; bioavailability and maximal plasma NSAID concentration after topical application are generally less than 5 and 15%, respectively, compared with equivalent oral administration. Product formulation has a dramatic impact on topical delivery success such as on drug penetration rate, skin irritation, and product stability. Therefore, it is not surprising that prescription-strength topical NSAIDs have only been available in the US since early 2008.

The art is replete with the ways of dealing with pain and inflammation, both in humans and animals. The medical literature and patents around the world describe many ways in which these conditions can be treated, with greater or lesser success in any given situation. Oral-administered dosage forms are one suitable, if not the primary, form of administration of analgesic and anti-inflammatory drugs. Oral administration is necessarily systemic, thus causing, in many instances, unwanted, adverse side effects. Another form of administration is topical where the drug is administered locally through the skin. One form of topical administration is by use of patches, which can take many different forms. This invention pertains to novel matrix-type patches containing piroxicam for the transdermal treatment of pain and inflammation.

It would be desirable to provide novel matrix patches for topical application of piroxicam and methods for the treatment of acute and chronic pain and inflammation therewith. The matrix patches of this invention have excellent drug penetration though the skin, meaning that more piroxicam is delivered thereby enabling small patches to be used to achieve the administration of a given, therapeutically effective amount of the piroxicam over a given period of time. This should result in better clinical efficacy and reduced side effects than with administration of comparable amounts of the piroxicam orally or systemically. In addition, the matrix patches of this invention have excellent physical and chemical stabilities, necessary for useful and commercially viable products. The matrix patches of this invention are extremely compatible with mammalian skin with little or no skin irritation.

SUMMARY OF THE INVENTION

This invention relates to novel matrix patches for the topical (i.e., transdermal) administration of piroxicam and methods for the localized treatment of acute and chronic pain and inflammation, and their related symptoms. This invention is predicated on part on the discovery that the use of a minimal number of components on a transdermal patch not only provides for an acceptable therapeutic patch but also effectively delivers the piroxicam effectively to the patient. It is contemplated that the matrix patches of this invention have greater stability compared to other matrix patches containing the same active ingredient. Specifically, in one aspect, the matrix consists essentially of a pharmaceutically effective amount of piroxicam in an acrylic copolymer self-adhesive base, wherein said base further includes petrolatum, polyvinylpyrrolidone, and either dimethyl isosorbide and/or a monoalkyl ether of diethylene glycol. The matrix patches of this invention deliver the piroxicam to the site or sites where it is intended to be absorbed locally over a given period of time to achieve the beneficial effects thereof. The patches may be prepared for prompt or immediate release of the piroxicam over time as it eludes from the matrix patch or, if desired, for controlled or sustained release over a longer period of time.

In its broadest aspects, this invention relates to novel matrix patches that have a therapeutically effective amount of piroxicam in a self-adhesive matrix that is placed in contact with the skin. The matrix patches of this invention show excellent penetration of the piroxicam through the skin, thus allowing effective transdermal administration of the piroxicam locally to the site or sites where the pain and/or inflammation occurs. The piroxicam is thus administered locally so as to minimize, to the extent possible, unwanted, adverse side effects that might arise from systemic administration.

The matrix patches of this invention are useful in the localized treatment of acute and chronic pain and inflammation associated with rheumatoid arthritis, osteoarthritis, inflammatory arthropathies, gout and pseudo-gout, dysmenorrhea, metastatic bone pain, headache and migraine, postoperative pain, post-herpetic neuralgia, neuropathic pains, sports injuries, soft-tissue injuries, strains, sprains, contusions, tendonitis or bursitis of the shoulder, elbow, wrist or knee, Carpal tunnel syndrome, lateral epicondylosis, low back pains and injury, and the like.

DETAILED DESCRIPTION OF SPECIFIC EMBODIMENTS OF THE INVENTION

As noted above, the novel matrix patches of this invention employ a minimal amount of components to achieve efficacious results thereby eliminating any potential adverse effects arising from conventional matrix patches. Accordingly, as used herein the term "consisting essentially of" means excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like.

The novel matrix patches of this invention have a removable covering layer (sometimes called a release layer or a releasable liner), a compatible backing layer, and a piroxicam-containing self-adhesive matrix layer in between. The self-adhesive matrix layer has about 0.1% to about 15%, preferably about 1% to about 5%, of piroxicam in an acrylate copolymer self-adhesive base, such as a Duro-Tak polymer available from National Starch and Chemical Company, Zutphen, Holland (preferably Duro-Tak 387-2052). In some embodiments, the % weight of peroxicam in the self-adhesive matrix layer is about 0.7 weight %, or about 1.1 weight %, or about 1.5 weight %, or about 1.7 weight %, or about 1.8 weight %, or about 2 weight %, or about 2.2 weight %, or about 2.4 weight %, or about 2.9 weight %, or about 3.1 weight %. The matrix also includes petrolatum (as a filler), polyvinylpyrrolidone K-30 (as a crystallization inhibitor), and either dimethyl isosorbide and/or a monoalkyl ether of diethylene glycol (e.g., the monoethyl ether of diethylene glycol) (as a penetration enhancer). The acrylate copolymer self-adhesive base also includes about 0.1% to about 50% petrolatum, preferably about 1% to about 10%, about 0.1% to about 35% polyvinylpyrrolidone K-30, preferably about 1% to about 10%, and about 0.1% to about 50%, preferably about 1% to about 20%, of either dimethyl isosorbide or a monoalkyl ether of diethylene glycol (e.g., the monoethyl ether of diethylene glycol) with the balance being the acrylic copolymer self-adhesive base. The above chosen ingredients are miscible at elevated temperatures (higher than 50° C.), necessary for processing.

Any suitable covering layer or backing layer that is compatible with the formulation of the matrix may be used. "Suitable", in this context, means that the layer is made from a material that is compatible with the matrix layer and prevents the matrix layer from degrading during storage before use and, with regard to the backing layer that remains on during use, does not allow the matrix layer to exude or leak through that layer during use. In addition, the backing should adhere suitably to the matrix layer and not wrinkle during storage or otherwise cause the matrix layer to separate from the backing layer. "Compatible" as it relates to the backing layer refers to a material that is compatible with the manufacturing process (i.e. doesn't degrade or dissolve under the process conditions used) and is stable such that the piroxicam does not crystallize during a shelf-life of at least 12 months, and more preferable, at least 18 months. In use, the covering layer is removed to expose the self-adhesive matrix layer, which is applied face down to contact with and adhere to the skin in the area of desired use, thus allowing the piroxicam to migrate from the matrix layer to penetrate through the skin for as long as the patch remains on the skin (and the piroxicam is still in the matrix layer). As the patch may be exposed to light when on the skin, the backing layer is preferably capable of blocking ultraviolet light or, optionally, but less preferred, the matrix layer should contain a suitable, compatible ultraviolet blocking component. The backing layer desirably is skin-colored or close to skin-colored so it is less obvious when in place on an area of the skin that might be seen when normal clothing is worn (for example, on the elbow when a short-sleeve shirt or blouse is worn, or on the knee when shorts are worn).

The piroxicam and all other components of this invention are well known and commercially available, generally from multiple sources. These ingredients may be used in any chemical form known in the art to be suitable for use in pharmaceutical preparations, for example, piroxicam itself or any pharmaceutically acceptable derivative form or pro-drug thereof. As noted above, the Duro-Tak acrylic copolymer (preferably Duro-Tak 387-2052) can be obtained from National Starch and Chemical Company, Zutphen, Holland. Petrolatum (marketed under the trademark Protopet®) may be obtained from Sonneborn, Inc., Mahwah, N.J., for example, their Super White Protopet®. Polyvinylpyrrolidone K-30 may be obtained from International Specialty Products (ISP), Wayne, N.J. The dimethyl isosorbide may be obtained from Croda, Inc., Edison, N.J. The monoethyl ether of diethylene glycol (marketed under the trade mark Transcutol P®) may be obtained from Gattefosse, Saint-Priest Cedex, France. A suitable backing layer material is AR7261, a non-woven fabric coated on one side with MA-31 medical grade, acrylic pressure-sensitive adhesive, which backing layer material can be obtained from Adhesives Research, Inc., Glen Rock, Pa. In some embodiments, the backing layer material is 3M CoTran 9699 Single Coated Melt Brown Polyurethane Tape coated on one side with hypoallergenic pressure sensitive acrylate adhesive. A suitable covering layer material is a fluoropolymer coated polyester film, for example No. 9744 that can be obtained from 3M, St. Paul, Minn. Backings with sufficient adhesion to the chosen matrix materials or a pre-coated adhesive backing compatible with the matrix are appropriate.

The structure of the matrix patch is as schematically shown in FIG. 1 of Hsu et al. U.S. Pat. No. 5,989,586 (and similar disclosures in the prior art), which shows the backing layer, the covering layer (i.e., the release layer or releasable lining) and the matrix layer in between, and can be prepared as briefly described therein.

In one embodiment, the patches of this invention can be prepared by mixing the piroxicam and other matrix layer components at about 60° C. until all of the powder components are dissolved, then vortexing the mixture to ensure homogeneity, followed by a short heating period (also at about 60° C.) to remove any bubbles, and then casting the mixture as a film onto the backing layer. The covering layer is applied and the patches are cut into the desired size and shape and stored individually in an outer package.

In another embodiment, the matrix patches may be prepared by solvent casting by admixing the components in a suitable solvent. The solution is cast onto a substrate, backing member or releasable liner. In one embodiment, the solution is cast onto the backing layer. Both admixture and casting are preferably carried out at ambient temperature. Optionally, the material coated with the film is then baked at or above ambient temperature, for example a temperature in the range of about 40 to 130° C., for a time period in the range of 5 minutes to 70 minutes. Evaporation of the solvent leaves a drug-containing adhesive as a uniform film.

When the matrix patch is prepared according to this method, the wet composition refers to the composition containing the solvent. The wet composition has about 0.1 weight % to about 90 weight % of solvent. In certain embodiments, the solvent is tetrahydrofuran.

Solvents for the active component, carrier, or adhesive are selected based on biocompatibility as well as the solubility of the material to be dissolved, and where appropriate, interaction with the active component or agent to be delivered. For example, the ease with which the active component or agent is dissolved in the solvent and the lack of detrimental effects of the solvent on the active component or agent to be delivered are factors to consider in selecting the solvent. Aqueous solvents can be used to make matrices formed of water soluble polymers. Organic solvents will typically be used to dissolve hydrophobic and some hydrophilic polymers. Preferred organic solvents are volatile or have a relatively low boiling point or can be removed under vacuum and which are acceptable for administration to humans in trace amounts, such as tetrahydrofuran (THF). Other solvents, such as ethyl acetate, ethanol, methanol, dimethyl formamide (DMF), acetone, acetonitrile, methylene chloride, acetic acid, dimethyl sulfoxide (DMSO) and chloroform, and combinations thereof, also may be utilized. Preferred solvents are those rated as class 3 residual solvents by the Food and Drug Administration, as published in the Federal Register vol. 62, number 85, pp. 24301-24309 (May 1997).

The size of the patch in square centimeters is selected to both give the desired dosage of piroxicam over the time that the matrix patch is intended to be left in contact with the skin and to cover all or part of the localized area of inflammation. As to the desired dose of piroxicam delivered, this will depend both upon the penetration rate that any given matrix layer of this invention will have and the size of the matrix patch used. Both factors are well know in the art. The piroxicam-containing matrix layer can extend from side-to-side as shown in FIG. 1 of Hsu et al. or, if desired, a small non-piroxicam-containing self-adhesive layer having the same acrylic copolymer as the piroxicam-containing layer (e.g., Duro-Tak 387-2052), or other compatible pressure sensitive adhesive, can be cast around the perimeter of the patch before or after the piroxicam-containing layer is cast. In the latter instance, the matrix patch of this invention would have a structure similar to FIGS. 2 and 3 of Lipp et al. U.S. Pat. No. 5,904,931, but with only one matrix layer instead of two separate layers (that is, there would be no space between what is shown as 6 and 8 in Lipp et al., but there would be a non-piroxicam-containing pressure sensitive adhesive layer encircling the matrix layer of this invention as shown by Lipp et al.

The matrix patches of this invention are applied to the skin for the period of time to achieve the desired administration of the piroxicam (generally 8, 10 or 12 hours), depending in part upon the need of each particular individual and the transdermal dosage amount desired to be administered. Once the beneficial results have been attained, the individual may be placed on a maintenance regimen where the administration of the piroxicam will be administered periodically as needed to maintain those beneficial results without necessarily having the same administration of the piroxicam as when the therapy was initially undertaken. This, as would be expected, may vary from individual to individual.

The matrix patches of this invention are useful for localized treatment of acute and chronic pain and inflammation for use in humans and other mammals. In some embodiments the mammal is a human. In other embodiments the mammal is a mammal commonly used in a laboratory such as a mouse, a rat, or a dog.

EXAMPLES

In the following examples, all percents recited are percents by weight and the following abbreviations have the following meanings:

| | |
|---|---|
| cm = | Centimeters |
| mg = | Milligrams |
| sq. cm. = | square centimeters |

The matrix patches of this invention are exemplified by the following specific embodiments.

Example 1

Matrix Patch with Dimethyl Isosorbide

A transdermal matrix patch for treating acute and chronic pain and inflammation for use in humans and other mammals is prepared having a self-adhesive matrix layer containing 27.5 mg (1.1%) piroxicam, 86.4 mg (3.45%) petrolatum, 142.5 mg (5.7%) dimethyl isosorbide, and 55 mg (2.2%) polyvinylpyrrolidone in 2,188.7 mg (87.558%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 2

Matrix Patch with Monoethyl Ether of Diethylene Glycol

A transdermal matrix patch for treating acute and chronic pain and inflammation for use in humans and other mammals is prepared having a self-adhesive matrix layer containing 27.5 mg (1.1%) piroxicam, 86.4 mg (3.45%) petrolatum, 142.5 mg (5.7%) monoethyl ether of diethylene glycol, and 55 mg (2.2%) polyvinylpyrrolidone in 2,188.7 mg (87.558%) Duro-Tak 387-2052 acrylic copolymer self-adhesive base. As in Example 1, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 3

Matrix Patch with Dimethyl Isosorbide

A transdermal matrix patch for treating acute and chronic pain and inflammation for use in humans and other mammals is prepared having a self-adhesive matrix layer containing 37.5 mg (1.50%) piroxicam, 117.8 mg (4.71%) petrolatum, 194.3 mg (7.77%) dimethyl isosorbide, and 75 mg (3.0%) polyvinylpyrrolidone in 2,075.5 mg (83.02%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 4

Matrix Patch with Monoethyl Ether of Diethylene Glycol

A transdermal matrix patch for treating acute and chronic pain and inflammation for use in humans and other mammals is prepared having a self-adhesive matrix layer containing 37.5 mg (1.50%) piroxicam, 117.8 mg (4.71%) petrolatum, 194.3 mg (7.77%) monoethyl ether of diethylene glycol, and 75 mg (3.0%) polyvinylpyrrolidone in 2,075.5 mg (83.02%) Duro-Tak 387-2052 acrylic copolymer self-adhesive base. As in Example 3, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 5

Matrix Patch with Dimethyl Isosorbide

A transdermal matrix patch for treating acute and chronic pain and inflammation for use in humans and other mammals is prepared having a self-adhesive matrix layer containing 42.5 mg (1.70%) piroxicam, 133.5 mg (5.34%) petrolatum, 220.2 mg (8.81%) dimethyl isosorbide, and 85 mg (3.40%) polyvinylpyrrolidone in 2,018.9 mg (80.76%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 6

Matrix Patch with Monoethyl Ether of Diethylene Glycol

A transdermal matrix patch for treating acute and chronic pain and inflammation for use in humans and other mammals is prepared having a self-adhesive matrix layer containing 42.5 mg (1.70%) piroxicam, 133.5 mg (5.34%) petrolatum, 220.2 mg (8.81%) monoethyl ether of diethylene glycol, and 85 mg (3.40%) polyvinylpyrrolidone in 2,018.9 mg (80.76%) Duro-Tak 387-2052 acrylic copolymer self-adhesive base. As in Example 5, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 7

Matrix Patch with Dimethyl Isosorbide

A transdermal matrix patch for treating acute and chronic pain and inflammation for use in humans and other mammals is prepared having a self-adhesive matrix layer containing 45 mg (1.8%) piroxicam, 141.3 mg (5.65%) petrolatum, 233.1 mg (9.32%) dimethyl isosorbide, and 90 mg (3.60%) polyvinylpyrrolidone in 1,990.6 mg (79.62%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 8

Matrix Patch with Monoethyl Ether of Diethylene Glycol

A transdermal matrix patch for treating acute and chronic pain and inflammation for use in humans and other mammals is prepared having a self-adhesive matrix layer containing 45 mg (1.8%) piroxicam, 141.3 mg (5.65%) petrolatum, 233.1 mg (9.32%) monoethyl ether of diethylene glycol, and 90 mg (3.60%) polyvinylpyrrolidone in 1,990.6 mg (79.62%) Duro-Tak 387-2052 acrylic copolymer self-adhesive base. As in Example 7, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.).

Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 9

Matrix Patch with Dimethyl Isosorbide

A transdermal matrix patch for treating acute and chronic pain and inflammation for use in humans and other mammals is prepared having a self-adhesive matrix layer containing 50 mg (2%) piroxicam, 157 mg (6.28%) petrolatum, 259 mg (10.36%) dimethyl isosorbide, and 101 mg (4.05%) polyvinylpyrrolidone in 1,933 mg (77.31%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 10

Matrix Patch with Monoethyl Ether of Diethylene Glycol

A transdermal matrix patch for treating localized acute and chronic pain and inflammation for use in humans and other mammals is prepared having a self-adhesive matrix layer containing 50 mg (2%) piroxicam, 157 mg (6.28%) petrolatum, 259 mg (10.36%) monoethyl ether of diethylene glycol, and 101 mg (4.05%) polyvinylpyrrolidone in 1,933 mg (77.31%) Duro-Tak 387-2052 acrylic copolymer self-adhesive base. As in Example 9, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn. Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 11

Matrix Patch with Dimethyl Isosorbide

A transdermal matrix patch for treating acute and chronic pain and inflammation for use in humans and other mammals is prepared having a self-adhesive matrix layer containing 55 mg (2.2%) piroxicam, 172.7 mg (6.91%) petrolatum, 284.9 mg (11.4%) dimethyl isosorbide, and 110 mg (4.40%) polyvinylpyrrolidone in 1,877.4 mg (75.10%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 12

Matrix Patch with Monoethyl Ether of Diethylene Glycol

A transdermal matrix patch for treating acute and chronic pain and inflammation for use in humans and other mammals is prepared having a self-adhesive matrix layer containing 55 mg (2.2%) piroxicam, 172.7 mg (6.91%) petrolatum, 284.9 mg (11.4%) monoethyl ether of diethylene glycol, and 110 mg (4.40%) polyvinylpyrrolidone in 1,877.4 mg (75.10%) Duro-Tak 387-2052 acrylic copolymer self-adhesive base. As in Example 11, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches after casting are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 13

Matrix Patch with Dimethyl Isosorbide

A transdermal matrix patch for treating acute and chronic pain and inflammation for use in humans and other mammals is prepared having a self-adhesive matrix layer containing 60 mg (2.40%) piroxicam, 188.4 mg (7.54%) petrolatum, 310.8 mg (12.43%) dimethyl isosorbide, and 120 mg (4.80%) polyvinylpyrrolidone in 1,820.8 mg (72.83%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 14

Matrix Patch with Monoethyl Ether of Diethylene Glycol

A transdermal matrix patch for treating acute and chronic pain and inflammation for use in humans and other mammals is prepared having a self-adhesive matrix layer containing 60 mg (2.40%) piroxicam, 188.4 mg (7.54%) petrolatum, 310.8 mg (12.43%) monoethyl ether of diethylene glycol, and 120 mg (4.80%) polyvinylpyrrolidone in 1,820.8 mg (72.83%) Duro-Tak 387-2052 acrylic copolymer self-adhesive base. As in Example 13, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 15

Matrix Patch with Dimethyl Isosorbide

A transdermal matrix patch for treating acute and chronic pain and inflammation for use in humans and other mammals is prepared having a self-adhesive matrix layer containing 72.5 mg (2.9%) piroxicam, 227.7 mg (9.11%) petrolatum, 375.6 mg (15.02%) dimethyl isosorbide, and 145 mg (5.80%) polyvinylpyrrolidone in 1,679.3 mg (67.17%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 16

Matrix Patch with Monoethyl Ether of Diethylene Glycol

A transdermal matrix patch for treating acute and chronic pain and inflammation for use in humans and other mammals is prepared having a self-adhesive matrix layer containing 72.5 mg (2.9%) piroxicam, 227.7 mg (9.11%) petrolatum, 375.6 mg (15.02%) monoethyl ether of diethylene glycol, and 145 mg (5.80%) polyvinylpyrrolidone in 1,679.3 mg (67.17%) Duro-Tak 387-2052 acrylic copolymer self-adhesive base. As in Example 15, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 17

Matrix Patch with Dimethyl Isosorbide

A transdermal matrix patch for treating acute and chronic pain and inflammation for use in humans and other mammals is prepared having a self-adhesive matrix layer containing 77.5 mg (3.1%) piroxicam, 243.4 mg (9.73%) petrolatum, 401.5 mg (16.06%) dimethyl isosorbide, and 155 mg (6.20%) polyvinylpyrrolidone in 1,622.7 mg (64.91%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 18

Matrix Patch with Monoethyl Ether of Diethylene Glycol

A transdermal matrix patch for treating acute and chronic pain and inflammation for use in humans and other mammals is prepared having a self-adhesive matrix layer containing 77.5 mg (3.1%) piroxicam, 243.4 mg (9.73%) petrolatum, 401.5 mg (16.06%) monoethyl ether of diethylene glycol, and 155 mg (6.20%) polyvinylpyrrolidone in 1,622.7 mg (64.91%) Duro-Tak 387-2052 acrylic copolymer self-adhesive base. As in Example 17, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 19

Matrix Patch with Dimethyl Isosorbide

A transdermal matrix patch for treating acute and chronic pain and inflammation for use in humans and other mammals is prepared having a self-adhesive matrix layer containing 27.5 mg (11%) piroxicam, 101.8 mg (4.07%) petrolatum, 138.1 mg (5.52%) dimethyl isosorbide, and 126.5 mg (5.06%) polyvinylpyrrolidone in 2,106.2 mg (84.25%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 20

Matrix Patch with Monoethyl Ether of Diethylene Glycol

A transdermal matrix patch for treating acute and chronic pain and inflammation for use in humans and other mammals is prepared having a self-adhesive matrix layer containing 27.5 mg (11%) piroxicam, 101.8 mg (4.07%) petrolatum, 138.1 mg (5.52%) monoethyl ether of diethylene glycol, 126.5 mg (5.06%) polyvinylpyrrolidone in 2,106.2 mg (84.25%) Duro-Tak 387-2052 acrylic copolymer self-adhesive base. As in Example 19, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 21

Matrix Patch with Dimethyl Isosorbide

A transdermal matrix patch for treating acute and chronic pain and inflammation for use in humans and other mammals is prepared having a self-adhesive matrix layer containing 37.5 mg (1.50%) piroxicam, 138.8 mg (5.55%) petrolatum, 188.3 mg (7.53%) dimethyl isosorbide, and 172.5 mg (6.9%) polyvinylpyrrolidone in 1,963 mg (78.52%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 22

Matrix Patch with Monoethyl Ether of Diethylene Glycol

A transdermal matrix patch for treating acute and chronic pain and inflammation for use in humans and other mammals is prepared having a self-adhesive matrix layer containing 37.5 mg (1.50%) piroxicam, 138.8 mg (5.55%) petrolatum, 188.3 mg (7.53%) monoethyl ether of diethylene glycol, and 172.5 mg (6.9%) polyvinylpyrrolidone in 1,963 mg (78.52%) Duro-Tak 387-2052 acrylic copolymer self-adhesive base. As in Example 21, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 23

Matrix Patch with Dimethyl Isosorbide

A transdermal matrix patch for treating acute and chronic pain and inflammation for use in humans and other mammals is prepared having a self-adhesive matrix layer containing 42.5 mg (1.70%) piroxicam, 157.3 mg (6.29%) petrolatum, 213.4 mg (8.53%) dimethyl isosorbide, and 195.5 mg (7.82%) polyvinylpyrrolidone in 1,891.4 mg (75.66%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 24

Matrix Patch with Monoethyl Ether of Diethylene Glycol

A transdermal matrix patch for treating acute and chronic pain and inflammation for use in humans and other mammals is prepared having a self-adhesive matrix layer containing 42.5 mg (1.70%) piroxicam, 157.3 mg (6.29%) petrolatum, 213.4 mg (8.53%) monoethyl ether of diethylene glycol, and 195.5 mg (7.82%) polyvinylpyrrolidone in 1,891.4 mg (75.66%) Duro-Tak 387-2052 acrylic copolymer self-adhesive base. As in Example 23, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. The size of the patches after casting are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 25

Matrix Patch with Dimethyl Isosorbide

A transdermal matrix patch for treating acute and chronic pain and inflammation for use in humans and other mammals is prepared having a self-adhesive matrix layer containing 45 mg (1.8%) piroxicam, 166.5 mg (6.66%) petrolatum, 225.9 mg (9.04%) dimethyl isosorbide, and 207 mg (8.28%) polyvinylpyrrolidone in 1,855.6 mg (8.28%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 26

Matrix Patch with Monoethyl Ether of Diethylene Glycol

A transdermal matrix patch for treating acute and chronic pain and inflammation for use in humans and other mammals is prepared having a self-adhesive matrix layer containing 45 mg (1.8%) piroxicam, 166.5 mg (6.66%) petrolatum, 225.9 mg (9.04%) monoethyl ether of diethylene glycol, and 207 mg (8.28%) polyvinylpyrrolidone in 1,855.6 mg (8.28%) Duro-Tak 387-2052 acrylic copolymer self-adhesive base. As in Example 25, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 27

Matrix Patch with Dimethyl Isosorbide

A transdermal matrix patch for treating acute and chronic pain and inflammation for use in humans and other mammals is prepared having a self-adhesive matrix layer containing 50 mg (2%) piroxicam, 186 mg (7.44%) petrolatum, 251 mg (10.04%) dimethyl isosorbide, and 228 mg (9.12%) polyvinylpyrrolidone in 1,785 mg (71.4%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 28

Matrix Patch with Monoethyl Ether of Diethylene Glycol

A transdermal matrix patch for treating acute and chronic pain and inflammation for use in humans and other mammals is prepared having a self-adhesive matrix layer containing 50 mg (2%) piroxicam, 186 mg (7.44%) petrolatum, 251 mg (10.04%) monoethyl ether of diethylene glycol, and 228 mg (9.12%) polyvinylpyrrolidone in 1,785 mg (71.4%) Duro-Tak 387-2052 acrylic copolymer self-adhesive base. As in Example 27, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 29

Matrix Patch with Dimethyl Isosorbide

A transdermal matrix patch for treating acute and chronic pain and inflammation for use in humans and other mammals is prepared having a self-adhesive matrix layer containing 55 mg (2.2%) piroxicam, 203.5 mg (8.14%) petrolatum, 276.1 mg (11.04%) dimethyl isosorbide, and 253 mg (10.12%) polyvinylpyrrolidone in 1,712.4 mg (68.5%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 30

Matrix Patch with Monoethyl Ether of Diethylene Glycol

A transdermal matrix patch for treating acute and chronic pain and inflammation for use in humans and other mammals is prepared having a self-adhesive matrix layer containing 55 mg (2.2%) piroxicam, 203.5 mg (8.14%) petrolatum, 276.1 mg (11.04%) monoethyl ether of diethylene glycol, and 253 mg (10.12%) polyvinylpyrrolidone in 1,712.4 mg (68.5%) Duro-Tak 387-2052 acrylic copolymer self-adhesive base. As in Example 29, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 31

Matrix Patch with Dimethyl Isosorbide

A transdermal matrix patch for treating acute and chronic pain and inflammation for use in humans and other mammals is prepared having a self-adhesive matrix layer containing 60 mg (2.40%) piroxicam, 222 mg (8.88%) petrolatum, 301.2 mg (12.05%) dimethyl isosorbide, and 276 mg (11.04%) polyvinylpyrrolidone in 1,640.8 mg (65.63%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 32

Matrix Patch with Monoethyl Ether of Diethylene Glycol

A transdermal matrix patch for treating acute and chronic pain and inflammation for use in humans and other mammals is prepared having a self-adhesive matrix layer containing 60 mg (2.40%) piroxicam, 222 mg (8.88%) petrolatum, 301.2 mg (12.05%) monoethyl ether of diethylene glycol, and 276 mg (11.04%) polyvinylpyrrolidone in 1,640.8 mg (65.63%) Duro-Tak 387-2052 acrylic copolymer self-adhesive base. As in Example 31, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 33

Matrix Patch with Dimethyl Isosorbide

A transdermal matrix patch for treating acute and chronic pain and inflammation for use in humans and other mammals is prepared having a self-adhesive matrix layer containing 72.5 mg (2.9%) piroxicam, 268.3 mg (10.73%) petrolatum, 363.95 mg (14.56%) dimethyl isosorbide, and 333.5 mg (13.34%) polyvinylpyrrolidone in 1,461.8 mg (58.5%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 34

Matrix Patch with Monoethyl Ether of Diethylene Glycol

A transdermal matrix patch for treating acute and chronic pain and inflammation for use in humans and other mammals is prepared having a self-adhesive matrix layer containing 72.5 mg (2.9%) piroxicam, 268.3 mg (10.73%) petrolatum, 363.95 mg (14.56%) monoethyl ether of diethylene glycol, and 333.5 mg (13.34%) polyvinylpyrrolidone in 1,461.8 mg (58.5%) Duro-Tak 387-2052 acrylic copolymer self-adhesive base. As in Example 33, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 35

Matrix Patch with Dimethyl Isosorbide

A transdermal matrix patch for treating acute and chronic pain and inflammation for use in humans and other mammals is prepared having a self-adhesive matrix layer containing 77.5 mg (3.1%) piroxicam, 286.8 mg (11.47%) petrolatum, 389.1 mg (15.56%) dimethyl isosorbide, and 356.5 mg (14.26%) polyvinylpyrrolidone in 1,390.2 mg (55.61%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 36

Matrix Patch with Monoethyl Ether of Diethylene Glycol

A transdermal matrix patch for treating acute and chronic pain and inflammation for use in humans and other mammals is prepared having a self-adhesive matrix layer containing 77.5 mg (3.1%) piroxicam, 286.8 mg (11.47%) petrolatum, 389.1 mg (15.56%) monoethyl ether of diethylene glycol, and 356.5 mg (14.26%) polyvinylpyrrolidone in 1,390.2 mg (55.61%) Duro-Tak 387-2052 acrylic copolymer self-adhesive base. As in Example 35, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 37

Matrix Patch with Dimethyl Isosorbide

A transdermal matrix patch for treating acute and chronic pain and inflammation for use in humans and other mammals is prepared having a self-adhesive matrix layer containing 27.8 mg (1.1%) piroxicam, 103 mg (4.12%) petrolatum, 139 mg (5.56%) dimethyl isosorbide, and 126.3 mg (5.05%) polyvinylpyrrolidone in 2,104 mg (84.16%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 38

Matrix Patch with Monoethyl Ether of Diethylene Glycol

A transdermal matrix patch for treating acute and chronic pain and inflammation for use in humans and other mammals is prepared having a self-adhesive matrix layer containing 27.8 mg (1.1%) piroxicam, 103 mg (4.12%) petrolatum, 139 mg (5.56%) monoethyl ether of diethylene glycol, 126.3 mg (5.05%) polyvinylpyrrolidone in 2,104 mg (84.16%) Duro-Tak 387-2052 acrylic copolymer self-adhesive base. As in Example 37, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 39

Matrix Patch with Dimethyl Isosorbide

A transdermal matrix patch for treating acute and chronic pain and inflammation for use in humans and other mammals is prepared having a self-adhesive matrix layer containing 37.5 mg (1.5%) piroxicam, 139.1 mg (5.57%) petrolatum, 187.9 mg (7.52%) dimethyl isosorbide, and 170.6 mg (6.83%) polyvinylpyrrolidone in 1,964.9 mg (78.6%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 40

Matrix Patch with Monoethyl Ether of Diethylene Glycol

A transdermal matrix patch for treating acute and chronic pain and inflammation for use in humans and other mammals is prepared having a self-adhesive matrix layer containing 37.5 mg (1.5%) piroxicam, 139.1 mg (5.57%) petrolatum, 187.9 mg (7.52%) monoethyl ether of diethylene glycol, and 170.6 mg (6.83%) polyvinylpyrrolidone in 1,964.9 mg (78.6%) Duro-Tak 387-2052 acrylic copolymer self-adhesive base. As in Example 39, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 41

Matrix Patch with Dimethyl Isosorbide

A transdermal matrix patch for treating acute and chronic pain and inflammation for use in humans and other mammals is prepared having a self-adhesive matrix layer containing 42.5 mg (1.70%) piroxicam, 157.7 mg (6.31%) petrolatum, 212.9 mg (8.52%) dimethyl isosorbide, and 193.4 mg (7.74%) polyvinylpyrrolidone in 1,893.5 mg (75.74%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 42

Matrix Patch with Monoethyl Ether of Diethylene Glycol

A transdermal matrix patch for treating acute and chronic pain and inflammation for use in humans and other mammals is prepared having a self-adhesive matrix layer containing 42.5 mg (1.70%) piroxicam, 157.7 mg (6.31%) petrolatum, 212.9 mg (8.52%) monoethyl ether of diethylene glycol, and 193.4 mg (7.74%) polyvinylpyrrolidone in 1,893.5 mg (75.74%) Duro-Tak 387-2052 acrylic copolymer self-adhesive base. As in Example 41, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 43

Matrix Patch with Dimethyl Isosorbide

A transdermal matrix patch for treating acute and chronic pain and inflammation for use in humans and other mammals is prepared having a self-adhesive matrix layer containing 45 mg (1.8%) piroxicam, 167 mg (6.68%) petrolatum, 225.5 mg (9.02%) dimethyl isosorbide, and 204.8 mg (8.19%) polyvinylpyrrolidone in 1,857.9 mg (74.31%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 44

Matrix Patch with Monoethyl Ether of Diethylene Glycol

A transdermal matrix patch for treating acute and chronic pain and inflammation for use in humans and other mammals is prepared having a self-adhesive matrix layer containing 45 mg (1.8%) piroxicam, 167 mg (6.68%) petrolatum, 225.5 mg (9.02%) monoethyl ether of diethylene glycol, and 204.8 mg (8.19%) polyvinylpyrrolidone in 1,857.9 mg (74.31%) Duro-Tak 387-2052 acrylic copolymer self-adhesive base. As in Example 43, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 45

Matrix Patch with Dimethyl Isosorbide

A transdermal matrix patch for treating acute and chronic pain and inflammation for use in humans and other mammals is prepared having a self-adhesive matrix layer containing 50 mg (2%) piroxicam, 185.5 mg (7.42%) petrolatum, 250.5 mg (10.02%) dimethyl isosorbide, and 227.5 mg (9.1%) polyvinylpyrrolidone in 1,786.5 mg (71.46%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 46

Matrix Patch with Monoethyl Ether of Diethylene Glycol

A transdermal matrix patch for treating acute and chronic pain and inflammation for use in humans and other mammals is prepared having a self-adhesive matrix layer containing 50 mg (2%) piroxicam, 185.5 mg (7.42%) petrolatum, 250.5 mg (10.02%) monoethyl ether of diethylene glycol, and 227.5 mg (9.1%) polyvinylpyrrolidone in 1,786.5 mg (71.46%) Duro-Tak 387-2052 acrylic copolymer self-adhesive base. As in Example 45, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 47

Matrix Patch with Dimethyl Isosorbide

A transdermal matrix patch for treating acute and chronic pain and inflammation for use in humans and other mammals is prepared having a self-adhesive matrix layer containing 55 mg (2.2%) piroxicam, 204.1 mg (8.16%) petrolatum, 275.6 mg (11.02%) dimethyl isosorbide, and 250.3 mg (10.01%) polyvinylpyrrolidone in 1,715.2 mg (68.61%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. The size of the patches after casting are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 48

Matrix Patch with Monoethyl Ether of Diethylene Glycol

A transdermal matrix patch for treating acute and chronic pain and inflammation for use in humans and other mammals is prepared having a self-adhesive matrix layer containing 55 mg (2.2%) piroxicam, 204.1 mg (8.16%) petrolatum, 275.6 mg (11.02%) monoethyl ether of diethylene glycol, and 250.3 mg (10.01%) polyvinylpyrrolidone in 1,715.2 mg (68.61%) Duro-Tak 387-2052 acrylic copolymer self-adhesive base. As in Example 47, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 49

Matrix Patch with Dimethyl Isosorbide

A transdermal matrix patch for treating acute and chronic pain and inflammation for use in humans and other mammals is prepared having a self-adhesive matrix layer containing 60 mg (2.40%) piroxicam, 222.6 mg (8.90%) petrolatum, 300.6 mg (12.02%) dimethyl isosorbide, and 273 mg (10.92%) polyvinylpyrrolidone in 1,643.8 mg (65.75%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 50

Matrix Patch with Monoethyl Ether of Diethylene Glycol

A transdermal matrix patch for treating acute and chronic pain and inflammation for use in humans and other mammals is prepared having a self-adhesive matrix layer containing 60 mg (2.40%) piroxicam, 222.6 mg (8.90%) petrolatum, 300.6 mg (12.02%) monoethyl ether of diethylene glycol, and 273 mg (10.92%) polyvinylpyrrolidone in 1,643.8 mg (65.75%) Duro-Tak 387-2052 acrylic copolymer self-adhesive base. As in Example 49, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 51

Matrix Patch with Dimethyl Isosorbide

A transdermal matrix patch for treating acute and chronic pain and inflammation for use in humans and other mammals is prepared having a self-adhesive matrix layer containing 72.5 mg (2.9%) piroxicam, 269 mg (10.76%) petrolatum, 363.2 mg (14.53%) dimethyl isosorbide, and 329.9 mg (13.2%) polyvinylpyrrolidone in 1,465.4 mg (58.62%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 52

Matrix Patch with Monoethyl Ether of Diethylene Glycol

A transdermal matrix patch for treating acute and chronic pain and inflammation for use in humans and other mammals is prepared having a self-adhesive matrix layer containing 72.5 mg (2.9%) piroxicam, 269 mg (10.76%) petrolatum, 363.2 mg (14.53%) monoethyl ether of diethylene glycol, and 329.9 mg (13.2%) polyvinylpyrrolidone in 1,465.4 mg (58.62%) Duro-Tak 387-2052 acrylic copolymer self-adhesive base. As in Example 51, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 53

Matrix Patch with Dimethyl Isosorbide

A transdermal matrix patch for treating acute and chronic pain and inflammation for use in humans and other mammals is prepared having a self-adhesive matrix layer containing 77.5 mg (3.1%) piroxicam, 287.5 mg (11.5%) petrolatum, 388.3 mg (15.53%) dimethyl isosorbide, and 352.6 mg (14.11%) polyvinylpyrrolidone in 1,394.1 mg (55.76%) Duro-Tak 387-2052 acrylic copolymer self-adhesive base. The matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Example 54

Matrix Patch with Monoethyl Ether of Diethylene Glycol

A transdermal matrix patch for treating acute and chronic pain and inflammation for use in humans and other mammals is prepared having a self-adhesive matrix layer containing 77.5 mg (3.1%) piroxicam, 287.5 mg (11.5%) petrolatum, 388.3 mg (15.53%) monoethyl ether of diethylene glycol, and 352.6 mg (14.11%) polyvinylpyrrolidone in 1,394.1 mg (55.76%) Duro-Tak 387-2052 acrylic copolymer self-adhesive base. As in Example 53, the matrix layer is cast onto AR7261, a non-woven fabric coated on one side with MA-31 medical grade, acrylic pressure-sensitive adhesive (Adhesives Research, Inc., Glen Rock, Pa.) and is then covered with No. 9744 fluoropolymer coated polyester film (3M, St. Paul, Minn.). Alternatively, a 3M CoTran 9699 Single Coated Melt Brown Polyurethane Tape coated on one side with hypoallergenic pressure sensitive acrylate adhesive can be used for the backing. After casting, the patches are cut to 8 cm×12.5 cm (100 sq. cm). In use, the covering layer is removed and the matrix layer is placed in contact with the skin. The patches exhibit excellent penetration of the piroxicam through the skin during use on human subjects.

Alternative Procedure

In Examples 55-81, an alternative process for preparing the patches of this invention is provided. In the Examples that follow evaporation of the solvent occurs at or above ambient and preferably no higher than 50° C. above the boiling point of the solvent used. In one embodiment, the temperature at which solvent evaporation occurs is ambient temperature. In another embodiment, the temperature is approximately 15° C., or 20° C., or 25° C., or 30° C., or 35° C., or 40° C., or 45° C., or 50° C. above the boiling point of the solvent used. <<Inventors: What is the actual temperature above the boiling point>>

Example 55

Wet Composition with THF Solvent

A wet composition for use in making a transdermal matrix patch by the method of solvent casting is prepared by first making composition A containing 86.4 mg (2.85%) petrolatum, 55 mg (1.82%) polyvinylpyrrolidone and 2,188.7 mg (72.23%) Duro-Tak 387-2052 acrylic copolymer self-adhesive base. Composition A is then mixed at ambient temperature, and another mixture, composition B is prepared with 27.5 mg (0.91%) piroxicam, 142.5 mg (4.7%) monoethyl ether of diethylene glycol or dimethyl isosorbide, and 530.3 mg (17.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature.

Evaporation of the solvent leaves a drug-containing adhesive film. The matrix later is then covered with No. 9744 fluoropolymer coated polyester film (3M, St. Paul, Minn.).

Example 56

Wet Composition with THF Solvent

A wet composition for use in making a transdermal matrix patch by the method of solvent casting is prepared by first making composition A containing 117.8 mg (3.86%) petrolatum, 75 mg (2.46%) polyvinylpyrrolidone and 2,075.5 mg (68.08%) Duro-Tak 387-2052 acrylic copolymer self-adhesive base. Composition A is then mixed at ambient temperature, and another mixture, composition B is prepared with 37.5 mg (1.23%) piroxicam, 194.3 mg (6.37%) monoethyl ether of diethylene glycol or dimethyl isosorbide, and 548.8 mg (18%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 57

Wet Composition with THF Solvent

A wet composition for use in making a transdermal matrix patch by the method of solvent casting is prepared by first making composition A containing 133.5 mg (4.43%) petrolatum, 85 mg (2.82%) polyvinylpyrrolidone and 2,018.9 mg (67.03%) Duro-Tak 387-2052 acrylic copolymer self-adhesive base. Composition A is then mixed at ambient temperature, and another mixture, composition B is prepared with 42.5 mg (1.41%) piroxicam, 220.2 mg (7.31%) monoethyl ether of diethylene glycol or dimethyl isosorbide, and 512.1 mg (17%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 58

Wet Composition with THF Solvent

A wet composition for use in making a transdermal matrix patch by the method of solvent casting is prepared by first making composition A containing 141.3 mg (4.69%) petrolatum, 90 mg (2.99%) polyvinylpyrrolidone and 1,990.6 mg (66.09%) Duro-Tak 387-2052 acrylic copolymer self-adhesive base. Composition A is then mixed at ambient temperature, and another mixture, composition B is prepared with 45 mg (1.49%) piroxicam, 233.1 mg (7.74%) monoethyl ether of diethylene glycol or dimethyl isosorbide, and 512.1 mg (17%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 59

Wet Composition with THF Solvent

A wet composition for use in making a transdermal matrix patch by the method of solvent casting is prepared by first making composition A containing 157 mg (5.18%) petrolatum, 101.3 mg (3.34%) polyvinylpyrrolidone and 1,932.5 mg (63.78%) Duro-Tak 387-2052 acrylic copolymer self-adhesive base. Composition A is then mixed at ambient temperature, and another mixture, composition B is prepared with 50 mg (1.65%) piroxicam, 259 mg (8.55%) monoethyl ether of diethylene glycol or dimethyl isosorbide, and 530.4 mg (17.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 60

Wet Composition with THF Solvent

A wet composition for use in making a transdermal matrix patch by the method of solvent casting is prepared by first making composition A containing 172.7 mg (5.6%) petrolatum, 110 mg (3.56%) polyvinylpyrrolidone and 1,877.4 mg (60.83%) Duro-Tak 387-2052 acrylic copolymer self-adhesive base. Composition A is then mixed at ambient temperature, and another mixture, composition B is prepared with 55 mg (1.78%) piroxicam, 284.9 mg (9.23%) monoethyl ether of diethylene glycol or dimethyl isosorbide, and 586.4 mg (19%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 61

Wet Composition with THF Solvent

A wet composition for use in making a transdermal matrix patch by the method of solvent casting is prepared by first making composition A containing 188.4 mg (6.1%) petrolatum, 120 mg (3.89%) polyvinylpyrrolidone and 1,820.8 mg (58.99%) Duro-Tak 387-2052 acrylic copolymer self-adhesive base. Composition A is then mixed at ambient temperature, and another mixture, composition B is prepared with 60 mg (1.94%) piroxicam, 310.8 mg (10.07%) monoethyl ether of diethylene glycol or dimethyl isosorbide, and 586.4 mg (19%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 62

Wet Composition with THF Solvent

A wet composition for use in making a transdermal matrix patch by the method of solvent casting is prepared by first making composition A containing 227.7 mg (7.42%) petrolatum, 145 mg (4.73%) polyvinylpyrrolidone and 1,679.3 mg (54.75%) Duro-Tak 387-2052 acrylic copolymer self-adhesive base. Composition A is then mixed at ambient temperature, and another mixture, composition B is prepared with 72.5 mg (2.36%) piroxicam, 375.6 mg (12.24%) monoethyl ether of diethylene glycol or dimethyl isosorbide, and 567.5 mg (18.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 63

Wet Composition with THF Solvent

A wet composition for use in making a transdermal matrix patch by the method of solvent casting is prepared by first making composition A containing 243.4 mg (7.93%) petrolatum, 155 mg (5.05%) polyvinylpyrrolidone and 1,622.7 mg (52.9%) Duro-Tak 387-2052 acrylic copolymer self-adhesive base. Composition A is then mixed at ambient temperature, and another mixture, composition B is prepared with 77.5 mg (2.53%) piroxicam, 401.5 mg (13.09%) monoethyl ether of diethylene glycol or dimethyl isosorbide, and 567.5 mg (18.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 64

Wet Composition with THF Solvent

A wet composition for use in making a transdermal matrix patch by the method of solvent casting is prepared by first making composition A containing 101.8 mg (3.36%) petrolatum, 126.5 mg (4.17%) polyvinylpyrrolidone and 2,106.2 mg (69.5%) Duro-Tak 387-2052 acrylic copolymer self-adhesive base. Composition A is then mixed at ambient temperature, and another mixture, composition B is prepared with 27.5 mg (0.91%) piroxicam, 138.1 mg (4.56%) monoethyl ether of diethylene glycol or dimethyl isosorbide, and 530.3 mg (17.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 65

Wet Composition with THF Solvent

A wet composition for use in making a transdermal matrix patch by the method of solvent casting is prepared by first making composition A containing 138.8 mg (4.55%) petrolatum, 172.5 mg (5.66%) polyvinylpyrrolidone and 1,963 mg (64.39%) Duro-Tak 387-2052 acrylic copolymer self-adhesive base. Composition A is then mixed at ambient temperature, and another mixture, composition B is prepared with 37.5 mg (1.23%) piroxicam, 188.3 mg (6.17%) monoethyl ether of diethylene glycol or dimethyl isosorbide, and 548.8 mg (18%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 66

Wet Composition with THF Solvent

A wet composition for use in making a transdermal matrix patch by the method of solvent casting is prepared by first making composition A containing 157.3 mg (5.22%) petrolatum, 195.5 mg (6.49%) polyvinylpyrrolidone and 1,891.4 mg (62.79%) Duro-Tak 387-2052 acrylic copolymer self-adhesive base. Composition A is then mixed at ambient temperature, and another mixture, composition B is prepared with 42.5 mg (1.41%) piroxicam, 213.4 mg (7.08%) monoethyl ether of diethylene glycol or dimethyl isosorbide, and 512.1 mg (17%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 67

Wet Composition with THF Solvent

A wet composition for use in making a transdermal matrix patch by the method of solvent casting is prepared by first making composition A containing 166.5 mg (5.53%) petrolatum, 207 mg (6.87%) polyvinylpyrrolidone and 1,855.6 mg (61.61%) Duro-Tak 387-2052 acrylic copolymer self-adhesive base. Composition A is then mixed at ambient temperature, and another mixture, composition B is prepared with 45 mg (1.49%) piroxicam, 225.9 mg (7.5%) monoethyl ether of diethylene glycol or dimethyl isosorbide, and 512.1 mg (17%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 68

Wet Composition with THF Solvent

A wet composition for use in making a transdermal matrix patch by the method of solvent casting is prepared by first making composition A containing 186 mg (6.14%) petrolatum, 228 mg (7.52%) polyvinylpyrrolidone and 1,785 mg (58.91%) Duro-Tak 387-2052 acrylic copolymer self-adhesive base. Composition A is then mixed at ambient temperature, and another mixture, composition B is prepared with 50 mg (1.65%) piroxicam, 251 mg (8.28%) monoethyl ether of diethylene glycol or dimethyl isosorbide, and 530.3 mg (17.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 69

Wet Composition with THF Solvent

A wet composition for use in making a transdermal matrix patch by the method of solvent casting is prepared by first making composition A containing 203.5 mg (6.59%) petrolatum, 253 mg (8.2%) polyvinylpyrrolidone and 1,712.4 mg (55.48%) Duro-Tak 387-2052 acrylic copolymer self-adhesive base. Composition A is then mixed at ambient temperature, and another mixture, composition B is prepared with 55 mg (1.78%) piroxicam, 276.1 mg (8.95%) monoethyl ether of diethylene glycol or dimethyl isosorbide, and 586.4 mg (19%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 70

Wet Composition with THF Solvent

A wet composition for use in making a transdermal matrix patch by the method of solvent casting is prepared by first making composition A containing 222 mg (7.19%) petrolatum, 276 mg (8.94%) polyvinylpyrrolidone and 1,640.8 mg (53.16%) Duro-Tak 387-2052 acrylic copolymer self-adhesive base. Composition A is then mixed at ambient temperature, and another mixture, composition B is prepared with 60 mg (1.94%) piroxicam, 301.2 mg (9.76%) monoethyl ether of diethylene glycol or dimethyl isosorbide, and 586.4 mg (19%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 71

Wet Composition with THF Solvent

A wet composition for use in making a transdermal matrix patch by the method of solvent casting is prepared by first making composition A containing 268.3 mg (8.74%) petrolatum, 333.5 mg (10.87%) polyvinylpyrrolidone and 1,461.8 mg (47.65%) Duro-Tak 387-2052 acrylic copolymer self-adhesive base. Composition A is then mixed at ambient temperature, and another mixture, composition B is prepared with 72.5 mg (2.36%) piroxicam, 364.0 mg (11.86%) monoethyl ether of diethylene glycol or dimethyl isosorbide, and 567.5 mg (18.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 72

Wet Composition with THF Solvent

A wet composition for use in making a transdermal matrix patch by the method of solvent casting is prepared by first making composition A containing 286.8 mg (9.35%) petrolatum, 356.5 mg (11.62%) polyvinylpyrrolidone and 1,390.2 mg (45.32%) Duro-Tak 387-2052 acrylic copolymer self-adhesive base. Composition A is then mixed at ambient temperature, and another mixture, composition B is prepared with 77.5 mg (2.53%) piroxicam, 389.1 mg (12.68%) monoethyl ether of diethylene glycol or dimethyl isosorbide, and 567.5 mg (18.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 73

Wet Composition with THF Solvent

A wet composition for use in making a transdermal matrix patch by the method of solvent casting is prepared by first making composition A containing 103 mg (3.4%) petrolatum, 126.3 mg (4.17%) polyvinylpyrrolidone and 2,104 mg (69.43%) Duro-Tak 387-2052 acrylic copolymer self-adhesive base. Composition A is then mixed at ambient temperature, and another mixture, composition B is prepared with 27.8 mg (0.92%) piroxicam, 139 mg (4.59%) monoethyl ether of diethylene glycol or dimethyl isosorbide, and 530.3 mg (17.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 74

Wet Composition with THF Solvent

A wet composition for use in making a transdermal matrix patch by the method of solvent casting is prepared by first making composition A containing 139.1 mg (4.59%) petrolatum, 170.6 mg (5.63%) polyvinylpyrrolidone and 1,964.9 mg (64.84%) Duro-Tak 387-2052 acrylic copolymer self-adhesive base. Composition A is then mixed at ambient temperature, and another mixture, composition B is prepared with 37.5 mg (1.24%) piroxicam, 187.9 mg (6.2%) monoethyl ether of diethylene glycol or dimethyl isosorbide, and 530.4 mg (17.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 75

Wet Composition with THF Solvent

A wet composition for use in making a transdermal matrix patch by the method of solvent casting is prepared by first making composition A containing 157.7 mg (5.17%) petrolatum, 193.4 mg (6.34%) polyvinylpyrrolidone and 1,893.5 mg (62.11%) Duro-Tak 387-2052 acrylic copolymer self-adhesive base. Composition A is then mixed at ambient temperature, and another mixture, composition B is prepared with 42.5 mg (1.39%) piroxicam, 212.9 mg (6.98%) monoethyl ether of diethylene glycol or dimethyl isosorbide, and 548.8 mg (18%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 76

Wet Composition with THF Solvent

A wet composition for use in making a transdermal matrix patch by the method of solvent casting is prepared by first making composition A containing 167 mg (5.41%) petrolatum, 204.8 mg (6.63%) polyvinylpyrrolidone and 1,857.9 mg (60.19%) Duro-Tak 387-2052 acrylic copolymer self-adhesive base. Composition A is then mixed at ambient temperature, and another mixture, composition B is prepared with 45 mg (1.46%) piroxicam, 225.5 mg (7.3%) monoethyl ether of diethylene glycol or dimethyl isosorbide, and 586.4 mg (19%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 77

Wet Composition with THF Solvent

A wet composition for use in making a transdermal matrix patch by the method of solvent casting is prepared by first making composition A containing 185.5 mg (6.16%) petrolatum, 227.5 mg (7.55%) polyvinylpyrrolidone and 1,786.5 mg (59.31%) Duro-Tak 387-2052 acrylic copolymer self-adhesive base. Composition A is then mixed at ambient temperature, and another mixture, composition B is prepared with 50 mg (1.66%) piroxicam, 250.5 mg (8.32%) monoethyl ether of diethylene glycol or dimethyl isosorbide, and 512.1 mg (17%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 78

Wet Composition with THF Solvent

A wet composition for use in making a transdermal matrix patch by the method of solvent casting is prepared by first making composition A containing 204.1 mg (6.65%) petrolatum, 250.3 mg (8.16%) polyvinylpyrrolidone and 1,715.2 mg (55.91%) Duro-Tak 387-2052 acrylic copolymer self-adhesive base. Composition A is then mixed at ambient temperature, and another mixture, composition B is prepared with 55 mg (1.79%) piroxicam, 275.6 mg (8.98%) monoethyl ether of diethylene glycol or dimethyl isosorbide, and 567.5 mg (18.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 79

Wet Composition with THF Solvent

A wet composition for use in making a transdermal matrix patch by the method of solvent casting is prepared by first making composition A containing 222.6 mg (7.26%) petrolatum, 273 mg (8.9%) polyvinylpyrrolidone and 1,643.8 mg (53.59%) Duro-Tak 387-2052 acrylic copolymer self-adhesive base. Composition A is then mixed at ambient temperature, and another mixture, composition B is prepared with 60 mg (1.96%) piroxicam, 300.6 mg (9.8%) monoethyl ether of diethylene glycol or dimethyl isosorbide, and 567.5 mg (18.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 80

Wet Composition with THF Solvent

A wet composition for use in making a transdermal matrix patch by the method of solvent casting is prepared by first making composition A containing 269 mg (8.82%) petrolatum, 329.9 mg (10.82%) polyvinylpyrrolidone and 1,465.4 mg (48.07%) Duro-Tak 387-2052 acrylic copolymer self-adhesive base. Composition A is then mixed at ambient temperature, and another mixture, composition B is prepared with 72.5 mg (2.38%) piroxicam, 363.2 mg (11.91%) monoethyl ether of diethylene glycol or dimethyl isosorbide, and 548.8 mg (18%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

Example 81

Wet Composition with THF Solvent

A wet composition for use in making a transdermal matrix patch by the method of solvent casting is prepared by first making composition A containing 287.5 mg (9.32%) petrolatum, 352.6 mg (11.43%) polyvinylpyrrolidone and 1,394.1 mg (45.17%) Duro-Tak 387-2052 acrylic copolymer self-adhesive base. Composition A is then mixed at ambient temperature, and another mixture, composition B is prepared with 77.5 mg (2.51%) piroxicam, 388.3 mg (12.58%) monoethyl ether of diethylene glycol or dimethyl isosorbide, and 586.4 mg (19.5%) tetrahydrofuran. Composition B is mixed at ambient temperature until the Piroxicam is fully dissolved. Compositions A and B are then combined and mixed on a tumbler or rotator under capped conditions.

The wet composition can be cast onto a backing of 3M CoTran 9699 Single Coated Melt Brown Polyurethane Tape coated on one side with hypoallergenic pressure sensitive acrylate adhesive. Both admixture and casting are preferably carried out at ambient temperature. The material coated with the film is then heated at or above ambient temperature. Evaporation of the solvent leaves a drug-containing adhesive film. The matrix later is then covered with No. 9744 fluoropolymer coated polyester film (3M, St. Paul, Minn.).

The matrix patches with dimethyl isosorbide are slightly preferred over the patches with monoethyl ether of diethylene glycol as they are more easily removed from the skin when peeled off after 8 hours of use. This does not detract from the fact that the patches of both Example 1 and Example 2 exhibit excellent penetration of the piroxicam through the skin during use on human subjects.

The matrix patches of this invention are able to achieve the desirable aspects hereof with only the unique combination of components as described herein, and do not need, and do not have, other components (for example, the matrix patches of this invention do not include other solvents, glycols, hydroxide-releasing agents, triacetin, vitamin E, etc.).

While various embodiments of this invention have been described, it should be understood that various modifications and adaptations thereof will be apparent to one skilled in this art. Such modifications and adaptations are considered to be within the scope of this invention, which is limited only by the scope of the following claims.

What is claimed is:

1. A matrix patch for topical administration of piroxicam consisting of a removable covering layer, a compatible backing layer, and a piroxicam-containing self-adhesive matrix layer in between wherein the self-adhesive matrix layer includes a pharmaceutically effective amount of piroxicam in an acrylic copolymer self-adhesive base, wherein said base further includes petrolatum, polyvinylpyrrolidone, and either dimethyl isosorbide and/or a monoalkyl ether of diethylene glycol.

2. A matrix patch for topical administration of piroxicam consisting of a removable covering layer, a compatible backing layer, and a piroxicam containing self-adhesive matrix layer in between wherein the self-adhesive matrix layer consists essentially of a pharmaceutically effective amount of piroxicam in an acrylic copolymer self-adhesive base, wherein said base further includes petrolatum, polyvinylpyrrolidone, and dimethyl isosorbide.

3. A matrix patch for topical administration of piroxicam consisting of a removable covering layer, a compatible backing layer, and a piroxicam-containing self-adhesive matrix layer in between wherein the self-adhesive matrix layer consists essentially of a pharmaceutically effective amount of piroxicam in an acrylic copolymer self-adhesive base, wherein said base further includes petrolatum, polyvinylpyrrolidone, and monoethyl ether of diethylene glycol.

4. A matrix patch for topical administration of piroxicam consisting of a removable covering layer, a compatible backing layer, and a piroxicam-containing self-adhesive matrix layer in between wherein the self-adhesive matrix layer includes a pharmaceutically effective amount of piroxicam in an acrylic copolymer self-adhesive base, wherein said base further includes petrolatum, polyvinylpyrrolidone, a solvent, and either dimethyl isosorbide or a monoalkyl ether of diethylene glycol.

* * * * *